United States Patent [19]

Pikal et al.

[11] Patent Number: 5,612,315
[45] Date of Patent: Mar. 18, 1997

[54] PHARMACEUTICAL GROWTH HORMONE FORMULATIONS

[75] Inventors: Michael J. Pikal, Greenwood; Michael L. Roy, Indianapolis, both of Ind.

[73] Assignee: Eli Lilly and Company, Indianapolis, Ind.

[21] Appl. No.: 909,264

[22] Filed: Jul. 6, 1992

Related U.S. Application Data

[63] Continuation of Ser. No. 162,769, Mar. 1, 1988, abandoned.

[51] Int. Cl.$^6$ .................................................. A61K 38/00
[52] U.S. Cl. .............................. 514/21; 514/12; 514/970; 514/975
[58] Field of Search .............................. 514/12, 21, 970, 514/975

[56] References Cited

U.S. PATENT DOCUMENTS

| | | | |
|---|---|---|---|
| 3,940,480 | 2/1976 | Suenaga et al. | 514/12 |
| 4,327,086 | 4/1982 | Fukushima et al. | 424/177 |
| 4,340,589 | 7/1982 | Uemura et al. | 424/101 |
| 4,440,679 | 4/1984 | Fernandes et al. | 260/122 |
| 4,623,717 | 11/1986 | Fernandes et al. | 530/381 |
| 4,710,378 | 12/1987 | Ohtomo et al. | 424/89 |
| 4,816,568 | 3/1989 | Hamilton et al. | 514/970 |
| 5,096,885 | 3/1992 | Pearlman | 514/12 |

OTHER PUBLICATIONS

Webster's New Riverside Dictionary p. 1128.
Handbook of Pharmaceuticals Excipients, 177–180 (1987).
Physicians' Desk Reference, 970–971 (41st ed., 1987).
Physicians' Desk Reference, 1193–1194 (42d ed., 1988).
Pikal, et al., *Pharmaceutical Research*, 8, 427–436 (1991).
Drug Information '84, 1292–1294 (1984).
Pikal, "The Stability of Freeze Dried Proteins: The Effect of Excipients and Residual Water on the Chemical Decomposition and Aggregation of Freeze Dried Growth Hormone," Lecture, Jan. 31–Feb. 3, 1988.
Bangham, et al., *Molecular and Cellular Endocrinology*, 42, 269–282 (1985).
Biological Substances: International Standards and Reference Reagents 1986. 56–57 (1987).
Nanormon: Human Growth Hormone (Nordisk Insulinlaboratorium, Denmark).
Pharmaceutical Manufacturing Encyclopedia, 1380–1381 (2d ed., 1988).

*Primary Examiner*—Toni R. Scheiner
*Assistant Examiner*—Sheela J. Huff
*Attorney, Agent, or Firm*—James P. Leeds; Edward P. Gray

[57] ABSTRACT

Parenteral pharmaceutical formulations of human growth hormone, which are stabilized against aggregation, comprising biosynthetic human growth hormone, glycine, and mannitol. Methods of reducing aggregation of human growth hormone in parenteral formulations are also provided.

10 Claims, No Drawings

PHARMACEUTICAL GROWTH HORMONE FORMULATIONS

This application is a continuation of application Ser. No. 07/162,769, filed Mar. 1, 1988, now abandoned.

BACKGROUND OF THE INVENTION

Human growth hormone, also known as somatotropin, is an anterior pituitary hormone comprised of 191 amino acids and has a molecular weight of 22,000 daltons. It can be isolated from human pituitary glands or can be prepared biosynthetically as a result of advances in genetic engineering. At present there are two commercially available forms of the genetically engineered hormone, one of which is identical to native human growth hormone. The other form has an additional methionine residue at the N-terminus of the protein.

Human growth hormone is administered parenterally. A difficulty which has been encountered in the preparation of the pharmaceutical parenteral product has been that of aggregation of the human growth hormone upon storage. The present invention obviates this problem by providing parenteral formulations which are stabilized against aggregation of the human growth hormone.

SUMMARY OF THE INVENTION

The present invention is directed to a parenteral pharmaceutical formulation of human growth hormone. Said formulation comprises human growth hormone in admixture with aggregation stabilizing amounts of glycine and mannitol. Also disclosed and claimed is a method of reducing growth hormone aggregation in a parenteral formulation. Said method is effected by admixing human growth hormone with aggregation stabilizing amounts of glycine and mannitol.

DETAILED DESCRIPTION OF THE INVENTION

The parenteral formulation of the present invention is stabilized against the aggregation of human growth hormone. As mentioned earlier, human growth hormone is commercially available as the native material isolated from human pituitary glands or as two biosynthetically produced forms, one of which is identical to the native material and the other having an additional methionine residue at the N-terminus. For purposes of the present invention, any one or a combination of the three may be present in the parenteral formulation although the biosynthetically produced material which is identical to native human growth hormone is preferred.

The formulations of the present invention contain human growth hormone in admixture with aggregation stabilizing amounts of glycine and mannitol. By "aggregation stabilizing amounts" is meant those amounts of glycine and mannitol which, when admixed with human growth hormone, produce a formulation which is stabilized against aggregation. By "stabilized against aggregation" is meant that less aggregation of human growth hormone occurs when said hormone is formulated with aggregation stabilizing amounts of glycine and mannitol than when human growth hormone is formulated in the absence of both glycine and mannitol. A preferred parenteral formulation of human growth hormone which is stablized against aggregation is one containing human growth hormone, glycine and mannitol in a 1:1:5 weight ratio, respectively. While this is a preferred formulation, the skilled artisan will readily appreciate that amounts of any one of the three constituents outside of this preferred ratio containing aggregation stabilizing amounts of glycine and mannitol may produce additional preferred parenteral formulations of human growth hormone which are stabilized against aggregation.

The commercially available formulation is in the form of a lyophilized (i.e., freeze-dried) powder for reconstitution. Reconstitution of the formulation may be effected by the addition of a pharmaceutically acceptable vehicle therefor which may be aqueous or non-aqueous in nature. Examples of aqueous vehicles include water for injection, bacteriostatic water for injection, sterile water for injection and the like. Nonaqueous vehicles include corn oil, cottonseed oil, ethyl oleate, peanut oil, sesame oil and the like. The selection of the pharmaceutically acceptable vehicle will be merely a matter of choice for the skilled artisan, although the nonaqueous vehicles are more generally suited where prolonged duration of action is the goal. The actual product preparation is conventional in the art including, for example, container selection, sterilization, filling and sealing. Further information relating to parenteral product preparations may be obtained from standard treatises such as *Remington's Pharmaceutical Sciences*, 17th Edition (1985), which is incorporated herein by reference.

In order to further illustrate the present invention, the following evaluations were conducted.

Various formulations containing human growth hormone, glycine and mannitol were prepared in the weight ratios shown in Table I and were placed in parenteral vials and lyophilized. Two vials of each formulation were maintained at 40° centigrade and assayed at 14 days and 30 days for percent decomposition and percent aggregation of human growth hormone. The assay for decomposition was conducted by reverse phase high pressure liquid chromatography. The assay for aggregation of human growth hormone was by size exclusion chromatography. The results of these evaluations are shown in Table I.

TABLE I

| Formulation[a] | Percent Decomposition At Day Shown | | | Percent Aggregation At Day Shown | | |
|---|---|---|---|---|---|---|
| | 0 | 14 | 30 | 0 | 14 | 30 |
| 1:0:0 | 2.3 | 6.6 | 8.1 | 1 | 2.2 | 5.9 |
| 1:6:0 | 1.3 | 2.2 | 6.2[b] | 1.6 | 2.4 | 3.9 |
| 1:0:6 | 1.4 | 1.9[b] | 4.7 | 1.3 | 2.0[b] | 4.0 |
| 1:1:3 | 1.4 | 2.5 | — | 0.6 | 1.3 | — |
| 1:1:5 | 1.3 | 1.7 | 3.8 | 0.9 | 1.1 | 2.3 |

[a]Weight ratio of human growth hormone:glycine:mannitol
[b]only one of two samples assayed As can be clearly seen from the data shown in Table I, the formulation containing human growth hormone, glycine and mannitol in a weight ratio of 1:1:5, respectively exhibited less decomposition and aggregation at days 14 and 30 than the formulations lacking either or both of glycine and mannitol. The composition containing human growth hormone, glycine and mannitol in a weight ratio of 1:1:3, respectively exhibited less aggregation at day 14 than the formulations lacking either or both of glycine and mannitol.

We claim:

1. A parenteral pharmaceutical formulation of human growth hormone which is stabilized against aggregation consisting essentially of biosynthetic human growth hormone in admixture with aggregation stabilizing amounts of glycine and mannitol, wherein said human growth hormone, glycine, and mannitol are present in a weight ratio of about 1:1:3 to about 1:1:5, respectively.

2. The formulation of claim 1 wherein said human growth hormone, glycine and mannitol are present in a weight ratio of 1:1:5, respectively.

3. The formulation of claim 2 as a lyophilized powder.

4. The formulation of claim 3 additionally containing a pharmaceutically acceptable vehicle.

5. The formulation of claim 1 is a lyophilized powder.

6. A method of reducing aggregation of human growth hormone in a parenteral formulation which comprises preparing a parenteral pharmaceutical formulation of human growth hormone which is stabilized against aggregation consisting essentially of biosynthetic human growth hormone in admixture with aggregation stabilizing amounts of glycine and mannitol, wherein said biosynthetic human growth hormone, glycine, and mannitol are present in a weight ratio of about 1:1:3 to about 1:1:5, respectively.

7. The method of claim 6 wherein said human growth hormone, glycine and mannitol are present in a weight ratio of 1:1:5, respectively.

8. The method of claim 7 wherein the parenteral formulation is a lyophilized powder.

9. The method of claim 8 wherein the parenteral formulation additionally contains a pharmaceutically acceptable vehicle.

10. The method of claim 6 wherein the parenteral formulation is a lyophilized powder.

* * * * *